United States Patent [19]
Dean et al.

[11] Patent Number: 5,807,538
[45] Date of Patent: *Sep. 15, 1998

[54] TECHNETIUM-99M LABELED PEPTIDES FOR IMAGING INFLAMMATION

[75] Inventors: Richard T. Dean, Bedford, N.H.;
Robert S. Lees, Brookline, Mass.;
Scott Buttram, Derry, N.H.

[73] Assignee: Diatide, Inc., Londonderry, N.H.

[ * ] Notice: The term of this patent shall not extend beyond the expiration date of Pat. No. 5,552,525.

[21] Appl. No.: 484,774

[22] Filed: Jun. 7, 1995

Related U.S. Application Data

[62] Division of Ser. No. 266,178, Jun. 27, 1994, which is a continuation of Ser. No. 851,074, Mar. 13, 1992, abandoned.

[51] Int. Cl.⁶ .......................... A61K 51/00; A61M 36/14
[52] U.S. Cl. ...................... 424/1.69; 424/1.11; 424/1.65; 534/14; 530/300
[58] Field of Search ................................. 424/1.11, 1.65, 424/1.69, 9.1, 9.3, 9.4, 9.5; 534/10–16; 530/300, 324–330, 333, 334, 338

[56] References Cited

U.S. PATENT DOCUMENTS

| | | | |
|---|---|---|---|
| 4,615,876 | 10/1986 | Troutner et al. | 424/1.11 |
| 4,986,979 | 1/1991 | Morgan, Jr. et al. | 424/1.11 |
| 5,277,892 | 1/1994 | Rhodes | 424/1.69 |
| 5,376,356 | 12/1994 | Morgan, Jr. | 424/1.69 |
| 5,443,816 | 8/1995 | Zamora et al. | 424/9.1 |
| 5,506,208 | 4/1996 | Eyal et al. | 530/327 |
| 5,552,525 | 9/1996 | Dean | 530/326 |

*Primary Examiner*—Gary E. Hollinden
*Assistant Examiner*—Dameron Jones
*Attorney, Agent, or Firm*—Patricia A. McDaniels; Kevin E. Noonan

[57] ABSTRACT

This invention relates to radiolabeled peptides and methods for producing such peptides. Specifically, the invention relates to technetium-99m (Tc-99m) labeled leukocyte-binding peptides, methods and kits for making such peptides, and methods for using such peptides to image sites of infection and inflammation in a mammalian body.

12 Claims, No Drawings

TECHNETIUM-99M LABELED PEPTIDES FOR IMAGING INFLAMMATION

This is a divisional of application Ser. No. 08/266,178, filed Jun. 27, 1994, which is a file wrapper continuation of Ser. No. 07/851,074, filed Mar. 13, 1992, now abandoned.

BACKGROUND OF THE INVENTION

1. Field of the Invention

This invention relates to radiodiagnostic reagents and peptides, and methods for producing labeled radiodiagnostic agents. Specifically, the invention relates to technetium-99m (Tc-99m) labeled reagents, methods and kits for making such reagents, and methods for using such reagents to image sites of infection and inflammation in a mammalian body.

2. Description of the Prior Art

A variety of radionuclides are known to be useful for radioimaging, including $^{67}Ga$, $^{99m}Tc$ (Tc-99m), $^{111}In$, $^{123}I$, $^{125}I$, $^{169}Yb$ or $^{186}Re$. The sensitivity of imaging methods using radioactively-labeled peptides is much higher than other techniques known in the art, since the specific binding of the radioactive peptide concentrates the radioactive signal over the area of interest, for example, an inflammatory site.

There is a clinical need to be able to determine the location and/or extent of sites of focal or localized infection. In a substantial number of cases conventional methods of diagnosis (such as physical examination, x-ray, CT and ultrasonography) fail to identify such sites (e.g., an abscess). In some cases, biopsy may be resorted to, but is preferably avoided at least until it is necessary in order to identify the pathogen responsible for an abscess at a known location. Identifying the site of such "occult"' infection is important because rapid localization of the problem is critical to effective therapeutic intervention.

In the field of nuclear medicine, certain pathological conditions can be localized or the extent of such conditions determined by imaging the internal distribution of administered radioactively-labeled tracer compounds (i.e. radiotracers or radiopharmaceuticals) that accumulate specifically at the pathological site. However, an abscess may be caused by any one of many possible pathogens, so that a radiotracer specific for a particular pathogen would have limited scope. On the other hand, infection is almost invariably accompanied by inflammation, which is a general response of the body to tissue injury. Therefore, a radiotracer specific for sites of inflammation would be expected to be useful in localizing sites of infection caused by any pathogen.

One of the main phenomena associated with inflammation is the localization of leukocytes (white blood cells), usually monocytes and neutrophils, at the site of inflammation. A radiotracer specific for leukocytes would be useful in detecting leukocytes at the site of a localized infection. Currently approved nuclear medicine procedures for imaging sites of infection use either indium-111 labeled leukocytes ($^{111}In$-WBC) (see, e.g. Peters, 1992, J. Nucl. Med. 33: 65–67) or gallium-67 ($^{67}Ga$) citrate (see, e.g. Ebright et al., 1982, Arch. Int. Med. 142: 246–254). A major disadvantage of using $^{111}In$-labeled WBCs is that the preparation of the radiotracer requires sterile removal of autologous blood, sterile isolation of the leukocytes from the blood, sterile labeling of the leukocytes using conditions that do not damage the cells (since damaged WBC are taken up by the reticuloendothelial system when re-injected) and return (re-injection) of the (now labeled) leukocytes to the patient. Furthermore, a delay of 12 to 48 hours between injection and imaging may be required for optimal images. While Tc-99m labeled leukocytes have been used to shorten this delay period (see, e.g. Vorne et al., 1989, J. Nucl. Med. 30: 1332–1336), ex-corporeal labeling is still required. A preferred radiotracer would be one that does not require removal and manipulation of autologous blood components.

$^{67}Ga$-citrate can be administered by intravenous injection. However, this compound is not specific for sites of infection or inflammation. Moreover, a delay of up to 72 hours is often required between injection of the radiotracer and imaging. In addition, the γ-(gamma) emissions energies of $^{67}Ga$ are not well suited to conventional gamma cameras.

Radiolabeled monoclonal and polyclonal antibodies raised against human leukocytes (including monocytes, neutrophils, granulocytes and other) have been developed. Tc-99m labeled antigranulocyte monoclonal antibodies (see, e.g. Lind et al., 1990, J. Nucl. Med. 31: 417–473) and $^{111}In$-labeled non-specific human immunoglobulin (see, e.g. LaMuraglia et al., 1989, J. Vasc. Surg. 10: 20–28) have been tested for the detection of inflammation secondary to infection. $^{111}In$-labeled IgG shares the disadvantages of $^{111}In$-labeled WBC, in that 24–48 hours are required between injection and optimal imaging. In addition, all radiolabeled antibodies are difficult to produce and face protracted regulatory agency approval procedures as biologics.

Small readily synthesized molecules are preferred for routinely used radiopharmaceuticals. There is clearly a need for small synthetic molecules that can be directly injected into a patient and will image sites of infection and inflammation by localizing at sites where leukocytes have accumulated.

One class of compounds known to bind to leukocytes are chemotactic peptides that cause leukocytes to move up a peptide concentration gradient (see Wilkinson, 1988, Meth. Enzymol. 162: 127–132). These compounds bind to receptors on the surface of leukocytes with very high affinity. These peptides are derived from a number of sources, including complement factors, bacteria, tuftsin, elastin, fibrinopeptide B, fibrinogen Bβ, platelet factor 4 and others. Small synthetic peptides derived from these chemotactic compounds and radiolabeled would be very useful as radiotracers for imaging sites of inflammation in vivo.

Radiolabeled peptides have been reported in the prior art.

Zoghbi et al., 1981, J. Nucl. Med. 22: 32 (Abst) disclose formyl peptide chemotactic factors derived from bacteria coupled to $^{111}In$-labeled transferrin.

Jiang et al., 1982, Nuklearmedizin 21: 110–113 disclose a chemotactic formylated peptide radiolabeled with $^{125}I$.

Fischman et al., 1991, J. Nucl. Med. 32: 482–491 relates to chemotactic formyl peptide—$^{111}In$-labeled DTPA conjugates.

EPC 90108734.6 relates to chemotactic formyl peptide—$^{111}In$-labeled DTPA conjugates.

U.S. Pat. No. 4,986,979 relates to the use of radiolabeled chemotactic formyl peptides to radiolabel leukocytes ex-corporeally via a photoaffinity label.

PCT WO90/10463 relates to the use of radiolabeled chemotactic formyl peptides to radiolabel leukocytes ex-corporeally via a photoaffinity label.

The use of chelating agents for radiolabeling polypeptides, methods for labeling peptides and polypeptides with Tc-99m are known in the prior art and are disclosed in copending U.S. patent applications Ser. Nos. 07/653,012 now abandoned, which issued on Aug. 5, 1997 as U.S. Pat. No. 5,654,272 from continuation application Ser. No. 08/263,758, filed Jun. 22, 1994 and 07/807,062 which issued on Aug. 22, 1995 as U.S. Pat. No. 5,443,815, which are hereby incorporated by reference.

SUMMARY OF THE INVENTION

The present invention provides scintigraphic imaging agents that are radioactively-labeled peptides. The peptides of the invention are comprised of peptides that bind leukocytes and are covalently linked to a radioisotope complexing group wherein the complexing group binds a radioisotope.

In a first aspect of the present invention, radiolabeled peptides are provided capable of imaging site of inflammation in a mammalian body, such peptides comprising a specific binding peptide that binds to leukocytes, and a radiolabel-binding moiety of formula

wherein Cp is a protected cysteine residue and (aa) stands for an amino acid, and wherein the radiolabel-binding moiety is covalently linked to the specific binding peptides. In a preferred embodiment, the amino acid is glycine. In another preferred embodiment, the radiolabel-binding moiety is linked to the specific peptide via one or more amino acids.

In a second aspect, the present invention provides leukocyte-binding peptides that are covalently linked to a radiolabel-binding moiety having the following structure:

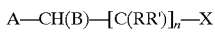

wherein A is H, HOOC, H$_2$NOC, or —NHOC; B is H, SH or NHR", where R" is H, lower alkyl or —C=O; X is SH or NHR", where R" is H, lower alkyl or —C=O; R and R' are independently H or lower alkyl; n is 0, 1 or 2; and: 1. where B is NHR", where R" is H, lower alkyl or —C=O, X is SH and n is 1 or 2; and 2. where X is NHR", where R" is H, lower alkyl or —C=O, B is SH and n is 1 or 2; 4. where B is H, A is HOOC, H$_2$NOC, or —NHOC, X is SH and n is 0 or 1; and wherein the thiol moiety is in the reduced form.

A peptide for imaging sites of inflammation within a mammalian body, comprising a specific binding peptide having an amino acid sequence comprising between 4 and 100 amino acids and wherein the peptide binds to leukocytes, and a radiolabel-binding moiety that forms a neutral complex with technetium-99m.

In yet another aspect, the present invention provides leukocyte-binding peptides that are covalently linked to a radiolabel-binding moiety having the following structure:

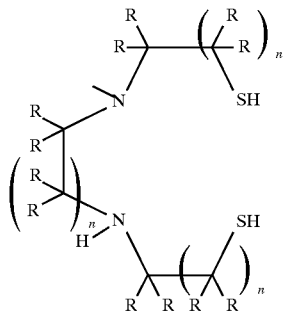

wherein each R is independently H, lower alkyl having 1 to 6 carbon atoms, phenyl, or phenyl substituted with lower alkyl or lower alkoxy, and wherein each n is independently 1 or 2. In a preferred embodiment, the radiolabel-binding moiety has the structure

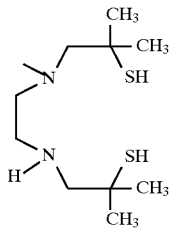

In an additional aspect of the invention, technetium-99m complexed peptides are provided, for imaging sites of inflammation within a mammalian body, comprising a leukocyte binding peptide having an amino acid sequence comprising between 4 and 100 amino acids and a radiolabel-binding moiety that forms a complex with technetium-99m, wherein the technetium-99m complexed peptide has a net charge of −1.

The invention also comprises complexes of the peptides of the invention with Tc-99m, kits for preparing the peptides of the invention radiolabeled with Tc-99m, methods for radiolabeling the peptides of the invention with Tc-99m and methods for using the radiolabeled peptides of the invention for imaging sites of infection or inflammation in mammalian body by gamma scintigraphy.

DETAILED DESCRIPTION OF THE INVENTION

The present invention provides Tc-99m labeled peptides for imaging target sites within a mammalian body that bind to leukocytes and are covalently linked to a radiolabel complexing group wherein the complexing group binds a radioisotope.

The peptides of this invention bind to leukocytes, preferably monocytes and neutrophils and most preferably to neutrophils. For purposes of this invention, the term "bind to leukocytes" is intended to mean that the peptides of the present invention are capable of accumulating at sites of infection or inflammation in mammalian body sufficient to allow detection of such sites by gamma scintigraphy.

In Cp(aa)Cp-containing peptides, the Cp is a protected cysteine where the S-protecting groups are the same or different and may be but not limited to:

—CH$_2$—aryl (aryl is phenyl or alkyl or alkyloxy substituted phenyl);

—CH—(aryl)$_2$, (aryl is phenyl or alkyl or alkyloxy substituted phenyl);

—C—(aryl)$_3$, (aryl is phenyl or alkyl or alkyloxy substituted phenyl);

—CH$_2$—(4-methoxyphenyl);

—CH—(4-pyridyl)(phenyl)$_2$;

—C(CH$_3$)$_3$

-9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

—CH$_2$—S—CH$_2$—phenyl

The preferred protecting group has the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Peptides of the present invention can be chemically synthesized in vitro. Peptides of the present invention can generally advantageously be prepared on an amino acid synthesizer. The peptides of this invention can be synthesized wherein the complexing group is covalently linked to the peptide during chemical in vitro synthesis, using techniques well known to those with skill in the art. Such peptides covalently-linked to the complexing group upon synthesis are advantageous because specific sites of covalent linkage can be determined therein.

In forming a complex of radioactive technetium with the peptides of this invention, the technetium complex, preferably a salt of Tc-99m pertechnetate, is reacted with the peptides of this invention in the presence of a reducing agent; in a preferred embodiment, the reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of the peptides of the invention that are to be labeled and a sufficient amount of reducing agent to label the peptide with Tc-99m. Alternatively, the complex may be formed by reacting the peptides of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. The reaction of the peptides of this invention with Tc-pertechnetate or preformed Tc-99m labile complex can be carried out in an aqueous medium at room temperature. The anionic complex which has a charge of [−1] is formed in the aqueous medium in the form of a salt with a suitable cation such as sodium cation, ammonium cation, mono-, di- or tri-lower alkyl amine cation, etc. Any conventional salt of the anionic complex with a pharmaceutically acceptable cation can be used in accordance with this invention.

In another embodiment of the present invention, the peptides of the invention that are to be labeled are reduced prior to labeling by incubating the peptides with a reducing agent. In a preferred embodiment, the reducing agent is stannous chloride. In an additional preferred embodiment, the reducing agent is a solid-phase reducing agent. The pre-reduced peptide is then labeled by reaction with a Tc-99m under reducing conditions or with pre-reduced Tc-99m or Tc-99m complex.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 3 and 100 amino acid residues, and are covalently linked to a radioisotope complexing group wherein the complexing group binds a radioisotope. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 2 hereinbelow.

Radioactively labeled peptides provided by the present invention are provided having a suitable amount of radioactivity. In forming the Tc-99m radioactive anionic complexes, it is generally preferred to form radioactive complexes in solutions containing radioactivity at concentrations of from about 0.01 millicurie (mCi) to 100 mCi per ml.

Technetium-labeled peptides provided by the present invention can be used for visualizing sites of inflammation, including abscesses and sites of "occult" infection. The Tc-99m labeled peptides provided by the present invention can also be used for visualizing sites of inflammation caused by tissue ischemia, including such disorders as inflammatory bowel disease and arthritis. In accordance with this invention, the technetium-labeled peptides or anionic complexes either as a complex or as a salt with a pharmaceutically acceptable cation are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Petide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzo-triazol-1-yl)-1,1,3,3-tetramethyluronium hexafluorophosphate/ hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Where appropriate N-α-formyl groups were introduced by treating the cleaved, deprotected peptide with acetic anhydride in 98% formic acid. Where appropriate the "pica"' group was introduced by conjugating picolylamine to a precursor peptide using diisopropylcarbodiimide and N-hydroxysuccinimide. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m 0.1 mg of a peptide prepared as in Example 1 was dissolved in 0.1 ml of 0.05M potassium phosphate buffer (pH 7.4). Tc-99m gluceptate was prepared by reconstituting a Glucoscan vial (E.I. DuPont de Nemours, Inc.) with 1.0 ml of Tc-99m sodium pertechnetate containing up to 200 mCi and allowed to stand for 15 minutes at room temperature. 25 $\mu$l of Tc-99m gluceptate was then added to the peptide and the reaction allowed to proceed at room temperature for 30 min and then filtered through a 0.2 $\mu$m filter.

The Tc-99m labeled peptide purity was determined by HPLC using a Vydak 218TP54 analytical column (RP-18, 5 micron, 220×4.6 mm) and eluted as described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

| Peptides | FABMS MH$^+$ | Radiochemical Yield | HPLC R$_1$ (min) |
|---|---|---|---|
| C$_{Mob}$GC$_{Acm}$PLYKKIIKKLLES (SEQ. ID NO.: 1) | 2028 | 97% | Bound |
| formyl-MLFC$_{Acm}$GC$_{Acm}$ (SEQ. ID NO.: 2) | 843 | 100% | 11.1,11.9[1] |
| C$_{Acm}$GC$_{Acm}$(VGVAPG)$_3$amide (SEQ. ID. NO.: 11) | 1865 | 100% | 17.7[1] |
| formyl-MIFLC$_{Acm}$GC$_{Acm}$ (SEQ. ID NO.: 3) | 957 | 100% | 11.4[1] |
| C$_{Acm}$GC$_{Acm}$TKPR (SEQ. ID NO.: 4) | 906.5 | 100% | 16.1[1] |
| formyl-MLFC$_{Acm}$GPica (SEQ. ID NO.: 5) | 760 | 100% | 10.9,12.2[1] |
| formyl-Nle-LF-Nle-YKC$_{Acm}$GC$_{Acm}$ (SEQ. ID NO.: 6) | 1230 | 97% | 15.6–16.8[2] |
| PicGC$_{Acm}$(VGVAPG)$_3$amide (SEQ. ID NO.: 12) | 1795 | 92% | 12.4[2] |
| PicGC$_{Acm}$(VPGVG)$_4$amide (SEQ. ID NO.: 13) | 1992 | 100% | 12.0[1] |
| PicGC$_{Acm}$PLYKKIIKKLLES (SEQ. ID NO.: 7) | 1910 | 81% | 12.9,13.3[3] |
| C$_{Acm}$GC$_{Acm}$PLYKKIIKKLLES (SEQ. ID NO.: 8) | 2093 | 96% | 12.6[3] |
| pGluGVNDNEEGFFSARC$_{Acm}$GC$_{Acm}$amide (SEQ. ID NO.: 9) | 1957 | 95% | 16.3,16.7[3] |
| PicGC$_{Acm}$GHRPLDKKREEAPSLRPAPPPISGGGYR (SEQ. ID NO.: 10) | 3377 | 94% | 11.3[3] |
| (VPGVG)$_4$GGGC$_{Acm}$GC$_{Acm}$amide (SEQ. ID NO.: 14) | 2231 | 67% | 11.2,11.5[3] |
| (VGVAPG)$_3$GGGC$_{Acm}$GC$_{Acm}$amide (SEQ. ID NO.: 15) | 2035 | 33% | 10.6[3] |
| AcC$_{Acm}$GC$_{Acm}$GGG(VPGVG)$_4$amide (SEQ. ID NO.: 16) | 2275 | 97% | 9.6,9.9[3] |
| AcC$_{Acm}$GC$_{Acm}$Aca(VPGVG)$_4$amide (SEQ. ID NO.: 17) | 2216 | 76% | 11.6,12.6[3] |

Ac = acetyl; Pic = picolinoyl (pyridine-2-carbonyl); Acm = acetamidomethyl; Mob = 4-Methoxybenzyl
Pica = picolylamine (2-(aminomethyl)pyridine); Aca = ε-aminocaproic acid
HPLC methods (indicated by superscript after R$_1$):
    general:    solvent A = 0.1% CF3COOH/H2O
                    solvent B$_{70}$ = 0.1% CF$_3$COOH/70% CH$_3$CN/H$_2$O
                    solvent B$_{90}$ = 0.1% CF$_3$COOH/90% CH$_3$CN/H$_2$O
                    solvent flow rate = 1 ml/min Vydak column=Vydak 218TP54 RP-18, 5$\mu$×220 mm×4.6 mm analytical column with guard column Brownlee column=Brownlee Spheri-5, RP-18 5$\mu$×220× 4.6 mm column

| Method 1: | Brownlee column | 100% A to 100% B$_{70}$ in 10 min |
| Method 2: | Vydak column | 100% A to 100% B$_{90}$ in 10 min |
| Method 3: | Vydak column | 100% A to 100% B$_{70}$ in 10 min |

It should be understood that the foregoing disclosure emphasizes certain specific embodiments of the invention and that all modifications or alternatives equivalent thereto are within the spirit and scope of the invention as set forth in the appended claims.

What is claimed is:

1. A complex formed by reacting a reagent comprising a leukocyte-binding chemotactic peptide covalently linked to a radiolabel-binding moiety selected from the group consisting of:

Cp(aa)Cp wherein Cp is a protected cysteine and (aa) is any primary α- or β-amino acid;

a radiolabel-binding moiety comprising a single thiol-containing moiety having a formula A—CH(B)—(C(RR'))$_n$—X wherein A is H, HOOC, H$_2$NOC, or NHOC;
B is H, SH, or NHR", where R" is H, lower alkyl, or —C=O;
X is SH or NHR", where R" is H, lower alkyl, or —C=O;
R and R' are independently H or lower alkyl;
n is 0, 1, or 2;
and where B is NHR", X is SH and n is 1 or 2;
where X is NHR", B is SH and n is 1 or 2;
where B is H, X is SH and n is 0 or 1;
and wherein the thiol moiety is in the reduced form;

and a radiolabel-binding moiety of formula

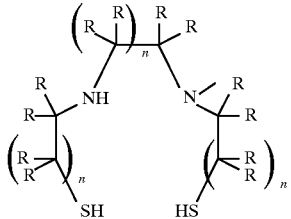

wherein each R is independently H, lower alkyl having one to six carbon atoms, phenyl, or phenyl substituted with lower alkyl or lower alkoxy, and wherein each n is independently one or 2, with technetium-99m in the presence of a reducing agent, wherein the complex is capable of accumulating at a site of inflammation in a mammalian body.

2. The complex of claim 1, wherein the reducing agent is selected from the group consisting of a dithionite ion, a stannous ion, a solid-phase reducing agent, and a ferrous ion.

3. The complex of claim 1, formed by ligand exchange of a prereduced technetium-99m complex.

4. A method for preparing an imaging agent for detecting infection or inflammation in a mammalian body comprising the steps of a) providing a reagent comprising a leukocyte-binding chemotactic peptide covalently linked to a radiolabel-binding moiety selected from the group consisting of Cp(aa)Cp wherein Cp is a protected cysteine and (aa) is any primary α- or β-amino acid;

a radiolabel-binding moiety comprising a single thiol-containing moiety having a formula

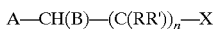

wherein
A is H, HOOC, H₂NOC, or NHOC;
B is H, SH, or NHR", where R" is H, lower alkyl, or —C=O;
X is SH or NHR", where R" is H, lower alkyl or —C=O;
R and R' are independently H or lower alkyl;
n is 0, 1, or 2;
and where B is NHR", X is SH and n is 1 or 2;
where X is NHR", B is SH and n is 1 or 2;
where B is H, X is SH and n is 0 or 1;
and wherein the thiol moiety is in the reduced form; and a radiolabel-binding moiety of formula

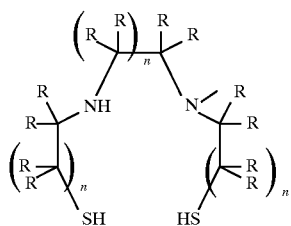

wherein each R is independently H, lower alkyl having one to six carbon atoms, phenyl, or phenyl substituted with lower alkyl or lower alkoxy, and wherein each n is independently one or 2, and b) reacting the reagent with technetium-99m in the presence of a reducing agent.

5. The method of claim 4, wherein the reducing agent is selected from the group consisting of a dithionite ion, a stannous ion, a ferrous ion, and a solid-phase reducing agent.

6. A method for preparing an imaging agent for detecting infection or inflammation in a mammalian body comprising the steps of a) providing a reagent comprising a leukocyte-binding chemotactic peptide covalently linked to a radiolabel-binding moiety selected from the group consisting of

Cp(aa)Cp wherein Cp is a protected cysteine and (aa) is any primary α- or β-amino acid;

a radiolabel-binding moiety comprising a single thiol-containing moiety having a formula

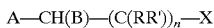

wherein
A is H, HOOC, H₂NOC, or NHOC;
B is H, SH, or NHR", where R" is H, lower alkyl, or —C=O;
X is SH or NHR", where R" is H, lower alkyl or —C=O;
R and R' are independently H or lower alkyl;
n is 0, 1, or 2;
and where B is NHR", X is SH and n is 1 or 2;
where X is NHR", B is SH and n is 1 or 2;
where B is H, X is SH and n is 0 or 1;
and wherein the thiol moiety is in the reduced form; and a radiolabel-binding moiety of formula

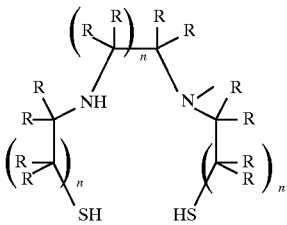

wherein each R is independently H, lower alkyl having one to six carbon atoms, phenyl, or phenyl substituted with lower alkyl or lower alkoxy, and wherein each n is independently one or 2, and b) labeling the reagent with technetium-99m by ligand exchange of a prereduced technetium-99m complex.

7. A complex formed by reacting technetium-99m with a reagent comprising a leukocyte-binding chemotactic peptide covalently linked to a radiolabel-binding moiety, wherein the technetium-99m complexed radiolabel-binding moiety has a net charge of −1, and wherein the complex is capable of accumulating at a site of inflammation in a mammalian body.

8. The complex of claim 7, formed by reacting the reagent with technetium-99m in the presence of a reducing agent.

9. The complex of claim 8, wherein the reducing agent is selected from the group consisting of a dithionite ion, a stannous ion, a solid-phase reducing agent, and a ferrous ion.

10. The complex of claim 7 formed by reacting the reagent with technetium-99m by ligand exchange of a prereduced technetium-99m complex.

11. A method for preparing an imaging agent for detecting infection or inflammation in a mammalian body comprising the steps of a) providing a reagent comprising a leukocyte-binding chemotactic peptide covalently linked to a radiolabel-binding moiety capable of forming a complex with technetium-99m having a net charge of −1; and b) labeling the reagent with technetium-99m by ligand exchange of a prereduced technetium-99m complex.

12. A complex formed by reacting technetium-99m with a reagent comprising a chemotactic peptide which binds to leukocytes covalently linked to a radiolabel-binding moiety, wherein the technetium-99m and the radiolabel-binding moiety form a neutral complex, and wherein the complex is capable of accumulating at a site of inflammation in a mammalian body.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1..3
      ( D ) OTHER INFORMATION: /label=Protected-Cys
         / note= "The thiol of the amino terminal cysteine
         is protected by a 4-methoxybebzyl group; the thiol
         of the cysteine at position 3 is protected by an ( x i ) SEQUENCE DESCRIPTION: SEQ ID NO:1:

Cys  Gly  Cys  Pro  Leu  Tyr  Lys  Lys  Ile  Ile  Lys  Lys  Leu  Leu  Glu  Ser
   1                   5                        10                       15

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 4..6
      ( D ) OTHER INFORMATION: /label=MODIFIED-CYS
         / note= "The thiol group of each cysteine is
         protected by an acetamidomethyl group; the amino
         terminal amine is formylated."

( x i ) SEQUENCE DESCRIPTION: SEQ ID NO:2:

Met  Leu  Phe  Cys  Gly  Cys
   1                   5

( 2 ) INFORMATION FOR SEQ ID NO:3:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 5..7
      ( D ) OTHER INFORMATION: /label=Modified-Cys
         / note= "The thiol group of each cysteine is
         protected by an acetamidomethyl group; the amino
         terminal amine is formylated."

( x i ) SEQUENCE DESCRIPTION: SEQ ID NO:3:

Met  Ile  Phe  Leu  Cys  Gly  Cys
   1                   5

( 2 ) INFORMATION FOR SEQ ID NO:4:

( i ) SEQUENCE CHARACTERISTICS:

(A) LENGTH: 7 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..3
(D) OTHER INFORMATION: /label=Modified-Cys
/ note= "The thiol group of each cysteine is
protected with an acetamidomethyl group."

(xi) SEQUENCE DESCRIPTION: SEQ ID NO:4:

Cys Gly Cys Thr Lys Pro Arg
1               5

(2) INFORMATION FOR SEQ ID NO:5:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 4..6
(D) OTHER INFORMATION: /label=Modified-Cys
/ note= "The thiol of the cysteine is protected by
an acetamidomethyl group; residue X =
2- aminomethylpyridine"

(xi) SEQUENCE DESCRIPTION: SEQ ID NO:5:

Met Leu Phe Cys Gly Xaa
1               5

(2) INFORMATION FOR SEQ ID NO:6:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1..4
(D) OTHER INFORMATION: /label=Norleucine
/ note= "Each X residue = norleucine; the amino
terminal amine of the amino terminal norleucine is
formylated."

(ix) FEATURE:
(A) NAME/KEY: Modified-site
(B) LOCATION: 7..9
(D) OTHER INFORMATION: /label=Modified-Cys
/ note= "The thiol of each cysteine residue is
protected by an acetamidomethyl group."

(xi) SEQUENCE DESCRIPTION: SEQ ID NO:6:

Xaa Leu Phe Xaa Tyr Lys Cys Gly Cys
1               5

(2) INFORMATION FOR SEQ ID NO:7:

(i) SEQUENCE CHARACTERISTICS:
(A) LENGTH: 16 amino acids
(B) TYPE: amino acid
(D) TOPOLOGY: linear (ii) MOLECULE TYPE: peptide ( i x ) FEATURE:
    ( A ) NAME/KEY: Modified-site
    ( B ) LOCATION: 1..3
    ( D ) OTHER INFORMATION: /label=Picolinoyl
        / note= "The amino terminal residue is
        pyridine-2- carbonyl; the thiol of the cysteine is
        protected by an acetamidomethyl group."

( x i ) SEQUENCE DESCRIPTION: SEQ ID NO:7:

```
Xaa  Gly  Cys  Pro  Leu  Tyr  Lys  Lys  Ile  Ile  Lys  Lys  Leu  Leu  Glu  Ser
1                   5                        10                       15
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..3
        ( D ) OTHER INFORMATION: /label=Modified-Cys
            / note= "The thiol group of each cyteine is
            protected by an acetamidomethyl group."

( x i ) SEQUENCE DESCRIPTION: SEQ ID NO:8:

```
Cys  Gly  Cys  Pro  Leu  Thr  Lys  Lys  Ile  Ile  Lys  Lys  Leu  Leu  Glu  Ser
1                   5                        10                       15
```

( 2 ) INFORMATION FOR SEQ ID NO:9:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..3
        ( D ) OTHER INFORMATION: /label=Picolinoyl
            / note= "The amino terminal residue is
            pyridine-2- carbonyl; the thiol of the cysteine
            residue is protected by an acetoamidomethyl ( x i ) SEQUENCE DESCRIPTION: SEQ ID NO:9:

```
Xaa  Gly  Cys  Gly  His  Arg  Pro  Leu  Asp  Lys  Lys  Arg  Glu  Glu  Ala  Pro
1                   5                        10                       15

Ser  Leu  Arg  Pro  Ala  Pro  Pro  Pro  Ile  Ser  Gly  Gly  Gly  Tyr  Arg
                    20                       25                       30
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 15..17
        ( D ) OTHER INFORMATION: /label=Modified-Cys
            / note= "The thiol of each cysteine is protected by
            an acetamidomethyl group; the carboxyl terminus is
            amidated; the amino terminal glutamic acid is -continued (x i) SEQUENCE DESCRIPTION: SEQ ID NO:10:

Glu Gly Val Asn Asp Asn Glu Glu Gly Phe Phe Ser Ala Arg Cys Gly
1               5                   10                      15

Cys (2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 4..6
        (D) OTHER INFORMATION: /label=MODIFIED-CYS
            / note= "The thiol group of each cysteine is
            protected by an acetamidomethyl group; the amino
            terminal amine is formylated."

(x i) SEQUENCE DESCRIPTION: SEQ ID NO:11:

Cys Gly Cys Val Gly Val Ala Pro Gly Val Gly Val Ala Pro Gly Val
1               5                   10                      15

Gly Val Ala Pro Gly
                20

(2) INFORMATION FOR SEQ ID NO:12:

(i) SEQUENCE CHARACTERISTICS:
        (A) LENGTH: 21 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1..3
        (D) OTHER INFORMATION: /label=Picolinoyl
            / note= "The amino terminal residue is
            pyridine-2- carbonyl; the thiol of the cysteine
            residue is protected by an acetoamidomethyl (x i) SEQUENCE DESCRIPTION: SEQ ID NO:12:

Xaa Gly Cys Val Gly Val Ala Pro Gly Val Gly Val Ala Pro Gly Val
1               5                   10                      15

Gly Val Ala Pro Gly
                20

(2) INFORMATION FOR SEQ ID NO:13:

(i) SEQUENCE CHARACTERISTICS:
        (A) LENGTH: 23 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1..3
        (D) OTHER INFORMATION: /label=Picolinoyl
            / note= "The amino terminal residue is
            pyridine-2- carbonyl; the thiol of the cysteine
            residue is protected by an acetoamidomethyl (x i) SEQUENCE DESCRIPTION: SEQ ID NO:13:

Xaa Gly Cys Val Pro Gly Val Gly Val Pro Gly Val Gly Val Pro Gly

```
        1               5                   10                  15
    Val   Gly   Val   Pro   Gly   Val   Gly
                            20
```

( 2 ) INFORMATION FOR SEQ ID NO:14:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 24..26
        ( D ) OTHER INFORMATION: /label=MODIFIED-CYS
            / note= "The thiol group of each cysteine is
            protected by an acetamidomethyl group; the carboxyl
            terminus is an amide."

( x i ) SEQUENCE DESCRIPTION: SEQ ID NO:14:

```
Val   Pro   Gly   Val   Gly   Val   Pro   Gly   Val   Gly   Val   Pro   Gly   Val   Gly   Val
1                       5                         10                        15
Pro   Gly   Val   Gly   Gly   Gly   Gly   Cys   Gly   Cys
                  20                        25
```

( 2 ) INFORMATION FOR SEQ ID NO:15:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 22..24
        ( D ) OTHER INFORMATION: /label=MODIFIED-CYS
            / note= "The thiol group of each cysteine is
            protected by an acetamidomethyl group; the carboxyl
            terminus is an amide."

( x i ) SEQUENCE DESCRIPTION: SEQ ID NO:15:

```
Val   Gly   Val   Ala   Pro   Gly   Val   Gly   Val   Ala   Pro   Gly   Val   Gly   Val   Ala
1                       5                         10                        15
Pro   Gly   Gly   Gly   Gly   Cys   Gly   Cys
                  20
```

( 2 ) INFORMATION FOR SEQ ID NO:16:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..3
        ( D ) OTHER INFORMATION: /label=MODIFIED-CYS
            / note= "The thiol group of each cysteine is
            protected by an acetamidomethyl group; the amino
            terminal amine is acetylated."

( x i ) SEQUENCE DESCRIPTION: SEQ ID NO:16:

```
Cys   Gly   Cys   Gly   Gly   Gly   Val   Pro   Gly   Val   Gly   Val   Pro   Gly   Val   Gly
1                       5                         10                        15
```

```
            Val  Pro  Gly  Val  Gly  Val  Pro  Gly  Val  Gly
                       20                       25
```

( 2 ) INFORMATION FOR SEQ ID NO:17:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..5
        ( D ) OTHER INFORMATION: /label=Modified-Cys
            / note= "The thiol of the cysteine is protected by
            an acetamidomethyl group; residue X =
            2- aminomethylpyridine"

( i x ) FEATURE:
        ( A ) NAME/KEY: Modified-site
        ( B ) LOCATION: 1..3
        ( D ) OTHER INFORMATION: /label=aminocaproate
            / note= "Residue Xaa = epsilon amino caproic
            acid."

( x i ) SEQUENCE DESCRIPTION: SEQ ID NO:17:

```
Cys  Gly  Cys  Xaa  Val  Pro  Gly  Val  Gly  Val  Pro  Gly  Val  Gly  Val  Pro
 1                  5                         10                        15
Gly  Val  Gly  Val  Pro  Gly  Val  Gly
                    20
```